(12) United States Patent
Sun (10) Patent No.: US 11,119,091 B2
(45) Date of Patent: Sep. 14, 2021

(54) METHOD AND DEVICE FOR AUTOMATICALLY TRACKING URINE

(71) Applicant: Shanghai Kohler Electronics, Ltd., Shanghai (CN)

(72) Inventor: Qintao Sun, Beijing (CN)

(73) Assignee: SHANGHAI KOHLER ELECTRONICS, LTD., Shanghai (CN)

( * ) Notice: Subject to any disclaimer, the term of this patent is extended or adjusted under 35 U.S.C. 154(b) by 17 days.

(21) Appl. No.: 16/299,773

(22) Filed: Mar. 12, 2019

(65) Prior Publication Data

US 2019/0285612 A1    Sep. 19, 2019

(30) Foreign Application Priority Data

Mar. 13, 2018   (CN) .......................... 201810205162.7

(51) Int. Cl.
| | |
|---|---|
| *G01N 33/493* | (2006.01) |
| *A61B 5/20* | (2006.01) |
| *A61B 10/00* | (2006.01) |
| *G16H 80/00* | (2018.01) |
| *E03D 11/13* | (2006.01) |

(52) U.S. Cl.
CPC ........... *G01N 33/493* (2013.01); *A61B 5/207* (2013.01); *A61B 10/007* (2013.01); *E03D 11/13* (2013.01); *G16H 80/00* (2018.01)

(58) Field of Classification Search
CPC ...... G01N 33/493; A61B 5/207; A61B 10/007
USPC .......................................................... 4/420
See application file for complete search history.

(56) References Cited

U.S. PATENT DOCUMENTS

| | | | |
|---|---|---|---|
| 10,383,606 B1* | 8/2019 | McCord | G01N 33/54386 |
| 2018/0303466 A1* | 10/2018 | Kashyap | H04N 5/332 |
| 2018/0372717 A1* | 12/2018 | Tu | A61M 25/0017 |
| 2019/0369085 A1* | 12/2019 | Tan | A61B 10/007 |
| 2020/0187863 A1* | 6/2020 | Tu | A61B 5/6891 |

FOREIGN PATENT DOCUMENTS

CN     105804189     7/2016

OTHER PUBLICATIONS (Isomura Atsushi) Estimation method of urinary volume and defecation properties based on visual volume intersection method using multi-view cameras; Summary of master's thesis, School of Information Science and Technology, Aichi Prefectural University, 2015; 2 pgs.
Notice of Preliminary Rejection KR Appln No. 2020052216880 dated Jul. 31, 2020, 5 pgs.
Foreign Action other than Search Report on Taiwanese Appl. Ser. No. 108102151 dated Mar. 30, 2020 (4 pages).

* cited by examiner

*Primary Examiner* — Huyen D Le
(74) *Attorney, Agent, or Firm* — Foley & Lardner LLP (57) ABSTRACT

A method of automatically tracing urine in a toilet that includes S1: acquiring an image of an interior of a toilet bowl (comprising an image of urine or an image simultaneously showing the urine and a collecting and tracing member of the toilet) through an image sensor; S2: identifying the urine or simultaneously identifying the urine and the collecting and tracing member through processing the image; and S3: implementing tracing movement to the urine by the collecting and tracing member. The method may, optionally, include S4: repeating S1, S2 and S3 until the collecting and tracing member coincides with the urine in the image.

20 Claims, 5 Drawing Sheets

METHOD AND DEVICE FOR AUTOMATICALLY TRACKING URINE

CROSS-REFERENCE TO RELATED PATENT APPLICATIONS

This application claims priority to and the benefit of Chinese Patent Application No. 201810205162.7, filed Mar. 13, 2018. The entire disclosure of the foregoing application, including the specification, drawings, claims, and abstract, is incorporated herein by reference in its entirety.

BACKGROUND

The present application relates generally to the field of urine detection, and more particularly, to a method and device of automatically tracking urine.

With the improvement of people's living standard, a smart toilet has gradually stepped into people's life. In addition to satisfying comfort requirements, the smart toilet is additionally provided with a health monitoring function that provides health data analysis through collecting a urine sample. However, using the urine collected from an inner surface of the toilet bowl for detection may have cross-contamination problems, which can affect the accuracy of the analysis of the health data. In order to avoid the cross-contamination problems affecting the accuracy of the health data analysis, the applicant's authorized patent 201610273915.9 discloses an automatic urine positioning method and device and a healthy smart toilet containing the same, in which it is pointed out that a non-contact temperature sensor driven by a stepping motor arranged on the left or right side wall of the toilet bowl can scan temperature in a mode of sector scanning within a certain angle range, and then the value X and/or Y in the coordinate (X, Y) of the position point of the urine in the toilet bowl can be calculated according to an angle and a tangent formula at the highest temperature.

According to the above said automatic urine positioning method and device and the healthy smart toilet containing the same, the cross contamination can be avoided through receiving the urine in the air. However, it has been found that there are still some shortcomings in the structure and the method in actual use, and since an optimal use effect may be difficult to achieve, the shortcomings can be summarized as set forth below.

(1) The structure and the positioning movement mode are complex, so that the stepping motor needs to drive the non-contract temperature sensor to move in a sector scanning mode.
(2) The coordinate of the position point of the urine needs to be calculated firstly, and then the urine-collection device will trace and collect the urine, which has higher requirement on the installation of the whole device and the accuracy of the urine collecting and tracing members.
(3) Solely identifying the urine might be greatly influenced by environment and other factors.

Thus, it can be seen that the existing automatic urine positioning method and device and the healthy smart toilet containing the same still have inconvenience and defects in structure, method and use, and need to be further improved. How to create a method and device of automatically tracing urine with a simple structure and tracing movement mode, a higher accuracy, and capacity of avoiding cross contamination have become a target urgently needing to be improved in the current industry.

SUMMARY

The technical problem to be solved by the present invention is to provide a method and device of automatically tracing urine, which are simple in structure and tracing movement mode, relative higher in accuracy, and capable of avoiding cross contamination.

In order to solve the above technical problems, the present invention adopts the following technical solutions.

According to one aspect, the present invention provides a method of automatically tracing urine applicable to a toilet provided with an image sensor and a urine-collection device on an inner side wall, wherein a liquid-collection head of the urine-collection device is a collecting and tracing member, and is used for tracing and collecting the urine at the same time.

According to one example, the method comprises:
Step 1 ("S1"), which includes acquiring an image of an interior of a toilet bowl through an image sensor, wherein the image of the interior of the toilet bowl comprises an image of urine or an image simultaneously showing the urine and the collecting and tracing member;
Step 2 ("S2"), which includes identifying the urine or simultaneously identifying the urine and the collecting and tracing member through processing the image acquired in S1; and
Step ("S3"), which includes implementing tracing movement to the urine by the collecting and tracing member in response to a result of the identification to the image acquired in S2.

Optionally, in S2, each pixel point in an acquired image can be compared with a threshold value set through an image characteristic of the urine to recognize the urine; or each pixel point in the acquired image can be compared with threshold values respectively set through image characteristics of the urine and the collecting and tracing member to recognize the urine and the collecting and tracing member.

Further, a background image can be firstly acquired before S1, where the background image is an image acquired when there is no urine nor the collecting and tracing member in the interior of the toilet bowl. Accordingly, in S2, the image can be processed to generate a difference image, where the difference image is a difference between the background image and the acquired image of the interior of the toilet bowl after the background image is acquired (e.g., the image captured in S1).

Further, in S2, binarization processing can be conducted on the difference image to generate a binary image; and a Hough transform can be conducted on the binary image in response to characteristic functions of the urine and the collecting and tracing member. For example, a column number of the urine and a column number of the collecting and tracing member can be identified according to a maximum value obtained from a Hough transform of two sets of characteristic functions.

Optionally, the method can further include Step 4 ("S4"), which includes repeating S1, S2, and S3 until the collecting and tracing member coincides with the urine in the image, and the collecting and tracing member stops moving.

Further, the characteristic function of the urine describes a vertical line, and the characteristic function of the collecting and tracing member describes a geometric curve related to a position and a shape of the collecting and tracing member.

According to another aspect, the present invention further provides a device of automatically tracing urine, which is a smart toilet, wherein an image sensor and a urine-collection device are installed on an inner side wall of the smart toilet, and a liquid-collection head of the urine-collection device is a collecting and tracing member, and is used for tracing and collecting the urine at the same time.

According to one example, the device of automatically tracing urine includes a memory, a processor, and a computer program that is stored in the memory and is executable on the processor, wherein the processor implements the above steps when (e.g., in response to) executing the computer program.

Optionally, the image sensor can be an infrared image sensor, a visible-light image sensor, or other suitable sensor.

Optionally, the image sensor can be installed on a left side wall or a right side wall of the smart toilet, and the urine-collection device is installed on the left side wall or the right side wall of the smart toilet. For example, the image sensor and the urine-collection device can be installed on opposite side walls.

Optionally, the image sensor can be installed on a front side wall or a rear side wall of the smart toilet, and the urine-collection device is installed on the front side wall or the rear side wall of the smart toilet. For example, one of the image sensor and the urine-collection device can be installed on the front side wall, and the other can be installed on the rear side wall.

Optionally, the collecting and tracing member can be provided with a color mark.

Optionally, the smart toilet can be replaced by a medical urine detection device.

Through the above technical solutions, the present invention provides at least the following advantages.

(1) The present invention relates to a method of automatically tracing urine based on image recognition, which uses the phenomenon that the urine, the urine-collection device, and the toilet have different image characteristics. The method employs the image sensor to collect the image of the interior of the toilet bowl, and recognizes the urine and the collecting and tracing member in the image to generate the motion function of the urine-collection device. The urine-collection device can automatically trace the urine through the method above, so that the urine can be automatically traced and collected by the urine-collection device when entering but not contacting the toilet, and thereby cross contamination of a urine sample is prevented and the accuracy of health data analysis is improved.

(2) When the collecting and tracing member of the urine-collection device coincides with the urine in the image, the urine-collection device stops moving. Through this method, a feedback control algorithm that simultaneously recognizes the urine and the collecting and tracing member is used, without calculating the specific position of the urine, thus the urine tracing accuracy by the collecting and tracing member is greatly improved, and the influence of the accuracy of the collecting and tracing member on urine tracing in the algorithm of solely identifying urine is removed. This method has higher accuracy and response speed.

(3) The difference image is used as an input of the control algorithm to eliminate the influences of the background difference and the sensor difference in the toilet on control.

(4) The device of tracing urine of the present invention uses the image sensor to acquire the position of the urine or the position information of the urine and the collecting and tracing member. Compared with a urine tracing device that moves in a sector scanning mode with the non-contact temperature sensor driven by the stepping motor, the device of tracing urine of the present invention has a simple structure and a simple tracing movement mode, a higher accuracy, and a faster response speed.

DETAILED DESCRIPTION

Figure 1:
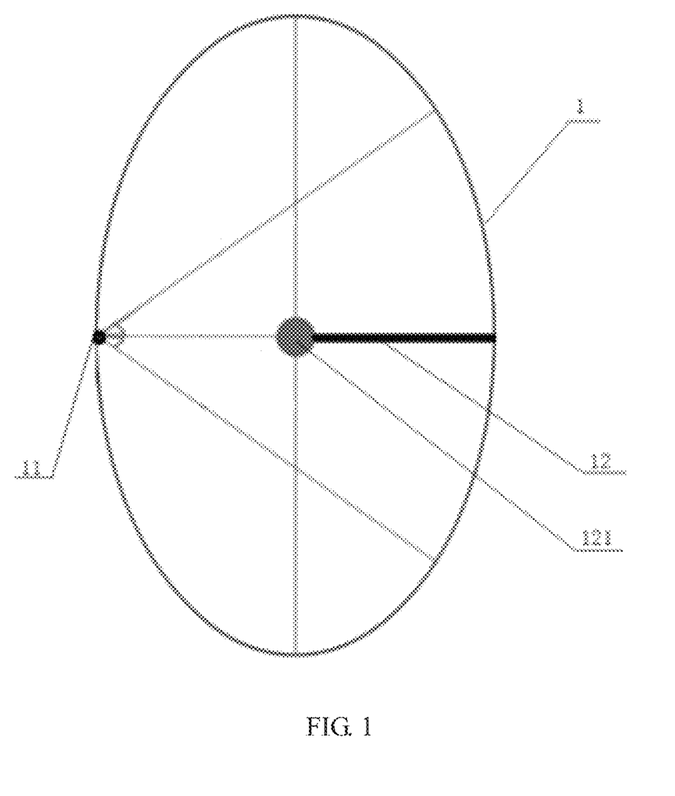
FIG. 1 is a structure diagram of a device of automatically tracing urine (toilet)

The present application relates to an automatic urine tracing device and method that employs image recognition, which, as shown in FIG. 1, is applicable to a toilet 1 provided with an image sensor 11 and a urine-collection device 12 on an inner side wall. Although the image sensor 11 and urine-collection device 12 are shown in FIG. 1 on opposing left and right side walls, they can be located on other portions of the toilet, such as opposing front and rear side walls. A liquid-collection head 121 of the urine-collection device 12 is a collecting and tracing member, and is used for collecting and tracing as well as identifying the urine at the same time. Several preferred automatic urine tracing methods are described in detail below.

Embodiment 1

Figure 2:
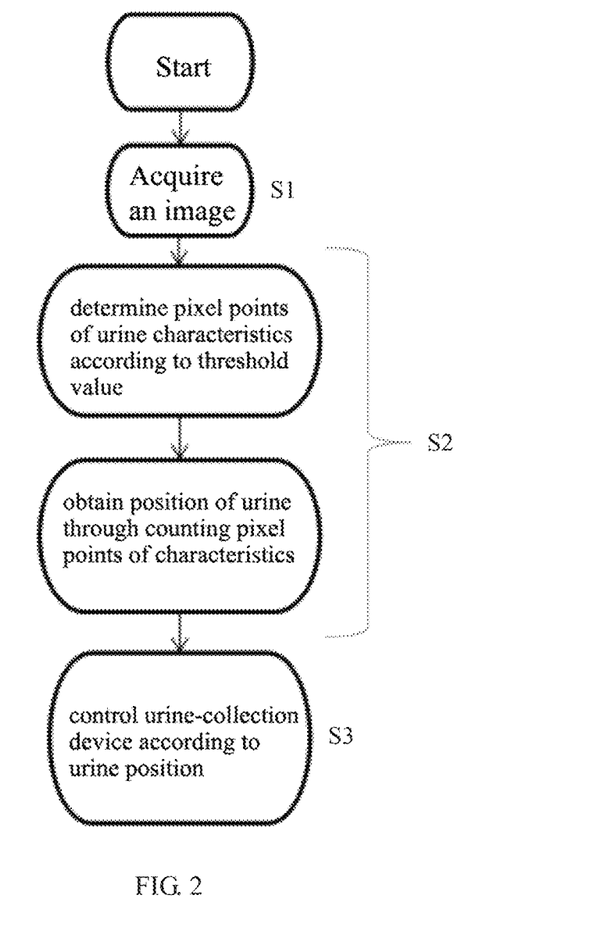
FIG. 2 is a flow chart of a method according to Embodiment 1.

FIG. 2 illustrates an example of an automatic urine tracing method that includes three steps. The method can be employed by a device for use with a toilet, such as the toilet 1, among other things.

Step 1 ("S1") involves acquiring an image of an interior of a toilet bowl through an image sensor, wherein the image of the interior of the toilet bowl comprises an image showing that there is urine in the toilet bowl.

Step 2 ("S2") involves recognizing the urine through image processing, which can include setting a threshold value according to an image characteristics of the urine; determining pixel points of the urine characteristics according to the threshold value; comparing each pixel of the image with the threshold value; and/or counting the pixels larger than the threshold value, wherein an area of pixels larger than the threshold value corresponds to the urine. S2 can involve calculating a position of the urine in the toilet bowl according to a position of the pixel with the largest value in the image.

Step 3 ("S3") involves controlling the urine-collection device according (e.g., in response) to the position of the urine, so as to make the collecting and tracing member implement urine tracing movement.

Embodiment 2

Figure 3:
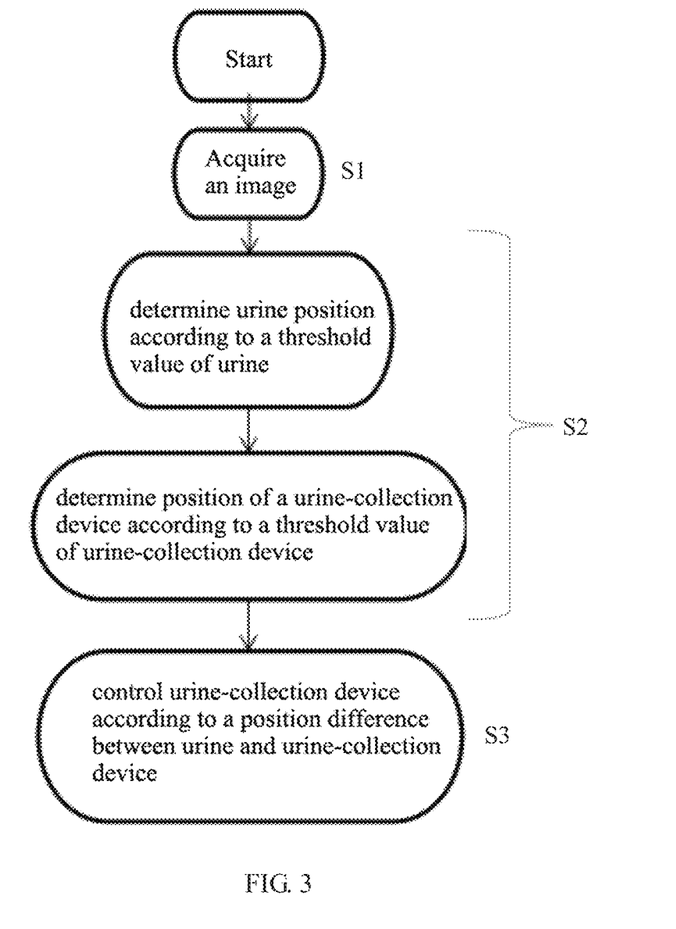
FIG. 3 is a flow chart of a method according to Embodiment 2.

FIG. 3 illustrates an example of an automatic urine tracing method that includes three steps. The method can be employed by a device for use with a toilet, such as the toilet 1, among other things.

Step 1 ("S1") involves acquiring an image of an interior of a toilet bowl through an image sensor, wherein the image of the interior of the toilet bowl comprises an image showing the urine and the collecting and tracing member.

Step 2 ("S2") involves identifying the urine and the collecting and tracing member through processing the image. More specifically, respectively setting threshold values for the urine and the collecting and tracing member, such as according to image characters of the urine and the collecting and tracing member; comparing the threshold values with each pixel point in the acquired image; counting the pixels larger than the threshold value of the collecting and tracing member, wherein an area of pixels larger than the threshold value corresponds to the collecting and tracing member; and/or counting the pixels which are larger than the threshold value of the urine and smaller than the threshold value of the urine-collection device, and an area of pixels within scope of the threshold value corresponds to the urine.

Step 3 ("S3") involves the collecting and tracing member moves towards the urine according to a location difference between the collecting and tracing member and the urine in the image.

Embodiment 3

Before S1 of Embodiment 1, the method further includes Step 0 ("S0").

S0 involves the image sensor firstly acquiring "n" groups of image data of the interior of the toilet bowl, then an average value of the image data is calculated (e.g., based on the "n" groups) as a background image and stored. The background image is an image showing no urine and no collecting and tracing member in the interior of the toilet bowl.

In S2, the image can be firstly processed to generate a difference image, and the difference image shows a difference between the acquired image of the interior of the toilet bowl and the background image after acquiring the background image.

Embodiment 4

Before S1 of Embodiment 2, the method further includes Step 0 ("S0").

S0 involves the image sensor firstly acquiring "n" groups of image data of an interior of the toilet bowl, then an average value of the image data is calculated (e.g., based on the "n" groups) as a background image and stored. The background image is an image showing no urine and no collecting and tracing member in the toilet bowl.

In S2, the image can be firstly processed to generate a difference image, and the difference image shows a difference between the acquired image of the interior of the toilet bowl and the background image after acquiring the background image.

Embodiment 5

In Embodiment 5, S2 of Embodiment 4 is replaced by subtracting background image data from the acquired image data every time to obtain a difference image. A binary image is generated, wherein the binary image is obtained by conducting binarization processing to the difference image; and the binarization processing method is to set a point in the image larger than the threshold value to 1 and a point in the image smaller than the threshold value to 0.

Hough transform is applied to (e.g., conducted on) the binary image according to characteristic functions of the urine and the collecting and tracing member, and column numbers corresponding to the urine and the collecting and tracing member respectively are identified according to a maximum value obtained from Hough transform of two sets of characteristic functions.

Figure 5:
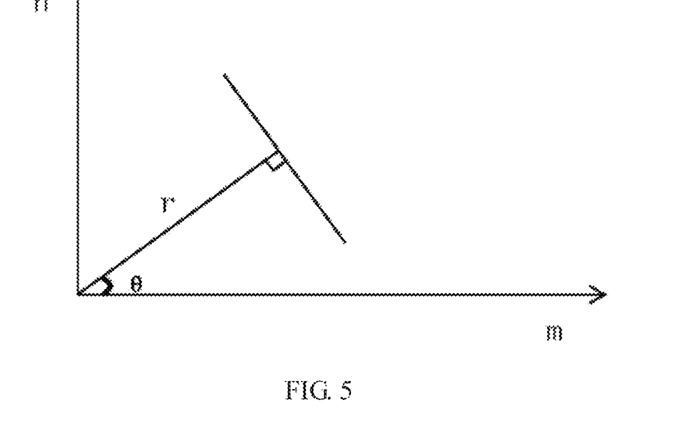
FIG. 5 is a principle diagram of a Hough transform.

As shown in FIG. 5, according to the principle of Hough transform, a characteristic equation of discrete points through which a line in the image passes is:

$$r=m*\cos(\theta)+n*\sin(\theta)$$

where r is a vertical distance from ordinate origin to the line, and θ is an included angle between r and a m-axis. That is, r is at the angle θ from the m-axis and an angle 90−θ from the n-axis, where the origin is the intersection of the m-axis and n-axis. FIG. 5 shows r intersecting the origin.

The characteristic function of the urine in the image describes a vertical line, and an angle θ of the characteristic equation of the urine is 0 degree.

An r value corresponding to all characteristic pixels of the urine is calculated and the number of occurrences of the same r value is counted. The r value with the most occurrences is the column number where the urine is located.

Figure 6:
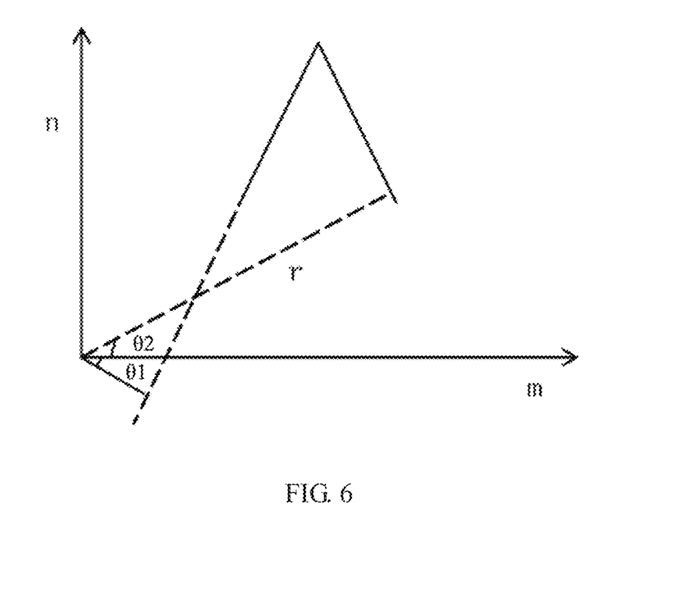
FIG. 6 is a principle diagram of a Hough transform of a urine-collection device.

It can be determined from FIG. 6 that a range of the angle θ in the characteristic equation of the urine-collection device is [θ1, θ2], the angle θ is divided into k parts, the r value of the characteristic pixel of the collecting and tracing member of the urine-collection device is calculated, and the number of occurrences of all r values is counted. The line corresponding to the r value with the most occurrences refers to the collecting and tracing member of the urine-collection device.

S3 is as follows: according to the location difference between the collecting and tracing member of the urine-collection device and the urine in the difference image, the urine-collection device moves towards the urine, specifically, according to a column difference ek between the recognized urine and the collecting and tracing member of the urine-collection device in the image, PI control (e.g., proportional-integral control) is conducted to the urine-collection device, and a control function is:

$$u(k)=Kp*ek+Ki*ek+u(k-1)$$

where $u(k)$ is the $k^{th}$ output of the urine-collection device, $u(k-1)$ is the $(k-1)^{th}$ output, Kp is a proportional coefficient, Ki is an integral coefficient, and ek is the $k^{th}$ difference.

Embodiment 6

Figure 4:
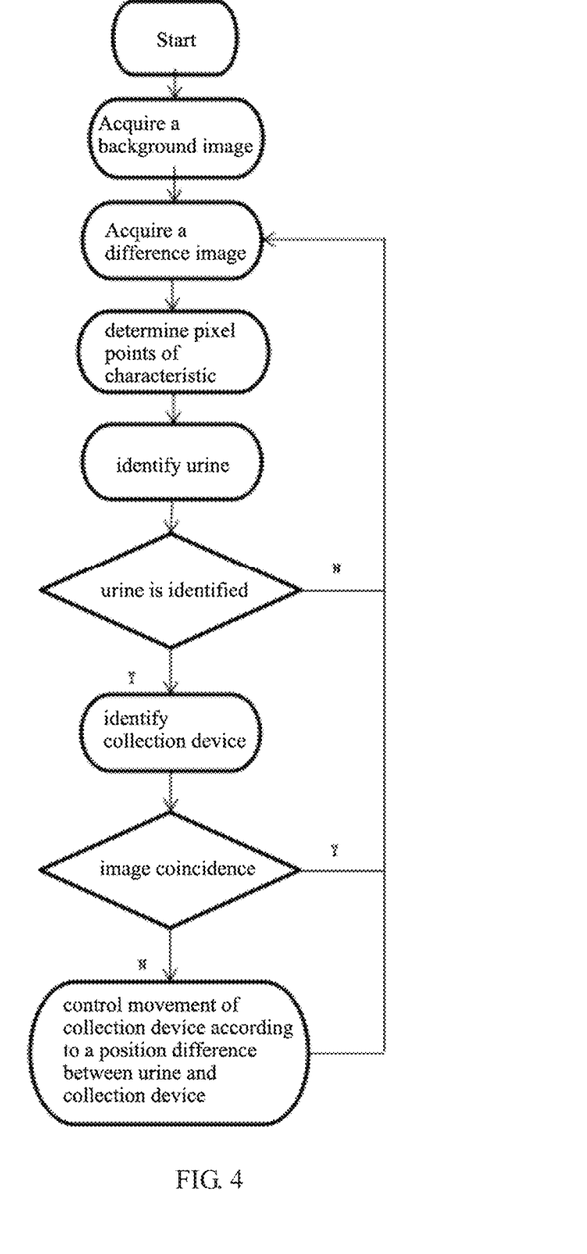
FIG. 4 is a flow chart of a method according to Embodiment 6.

On the basis of any one of the above embodiments (e.g., Embodiments 2, 4 and 5), a Step 4 ("S4") can be added, where S4 involves repeating S1, S2, and S3 until the collecting and tracing member coincides with the urine in the image, and the collecting and tracing member stops moving. FIG. 4 shows an example of such a method.

The present application further provides a device of automatically tracing urine, which is configured for use in a smart toilet. Referring back to FIG. 1, each of the image sensor 11 and the urine-collection device 12 is installed on an inner side wall of the smart toilet 1, and a liquid-collection head 121 of the urine-collection device 12 is configured as a collecting and tracing member, and is used for tracing and collecting the urine at the same time. The device of automatically tracing urine can also include a memory, a processor, and a computer program stored in the memory and executable on the processor, where the processor implements the steps of a method according to any of Embodiments 1-6 when executing the computer program.

The above said device of automatically tracing urine in a toilet can automatically trace the urine based on image recognition. By using a phenomenon that the urine, the urine-collection device, and the toilet have different image characteristics, an image sensor is used to collect an image of an interior of the toilet bowl, and the urine and the collecting and tracing member are recognized from the image to generate a motion function of the urine-collection device. The urine-collection device can automatically trace the urine through a method described above, so that the urine is automatically traced and collected by the urine-collection device when entering but not contacting the toilet bowl. That is, the urine collection device traces the urine within the bowl of the toilet and collects a sample of the urine prior to the urine contacting the bowl. Thereby, cross contamination of the urine sample can be prevented, and the accuracy of health data analysis is improved.

When the collecting and tracing member of the urine-collection device coincides with the urine in the image, the urine-collection device is configured to stop moving. Through this method, a feedback control algorithm is used for simultaneously identifying the urine and the tracing member, without having to calculate the specific position of the urine. Thus, the accuracy of tracing urine by the collecting and tracing member is greatly improved, and the influence of the accuracy of the tracing member on tracing urine related in the algorithm of solely identifying the urine is removed. This method has higher accuracy and response speed.

As a non-limiting example, the image sensor includes an infrared image sensor and/or a visible-light image sensor.

In at least one embodiment, the image sensor is arranged on the left side of the toilet bowl, and the urine-collection device is arranged on the right side of the toilet bowl. However, the present invention is not limited by the said installation method and/or structure, and those skilled in the art may understand that positions of the image sensor and the urine-collection device may also be interchanged, or both of the image sensor and the urine-collection device can be located on the left side or the right side of an inner wall of the toilet bowl, or the image sensor and the urine-collection device may be arranged on a front side or a back side of the inner wall of the toilet bowl. Alternatively, two sets of the urine-collection devices and the image sensors may be arranged (the first set of the urine-collection device and the image sensor are arranged on the left side or the right side of the toilet bowl, and the second set of the urine-collection device and the image sensor are arranged on the front side or the back side of the toilet bowl, which have higher matching accuracy, and the requirement on a liquid collection range of the tracing member of the urine-collection device will be greatly reduced).

Optionally, in order to cooperate with the image sensor to acquire a difference image, the collecting and tracing member of the urine-collection device can be provided with a color mark and/or other marks that can facilitate image recognition during use. A shape of the collecting and tracing member may also be any geometric shape such as a circle, a triangle, a square, etc.

The embodiments above are described with an example of a smart toilet. Certainly, those skilled in the art may understand that, in order to achieve the purpose of automatically tracing and detecting the urine, the above device does not need to be limited to the toilet, and may also be used in hospital. For example, the above method and device are also used in a container of a medical urine detection device in the hospital, and the purpose may be achieved by only replacing the container of the medical urine detection device with the toilet.

In conclusion, the urine-collection device may automatically trace the urine through a disclosed method based on image recognition according to the present invention, so that the urine may be automatically traced and collected by the urine-collection device when entering or passing through the toilet bowl, but prior to contacting the toilet bowl. In this way, cross contamination of the urine sample is prevented, and the accuracy of health data analysis is improved. Especially, motion control is conducted according to whether or not the collecting and tracing member of the urine-collection device is coincident with the urine in the image, without having to calculate (e.g., without calculating) the specific position of the urine. Thus, the accuracy of tracing urine by the collecting and tracing member is greatly improved, and the influence of the accuracy of the collecting and tracing member on tracing urine in the algorithm of solely identifying the urine is removed. The method has higher accuracy and response speed, and is suitable for popularization and application.

The foregoing is merely preferred embodiments of the present invention without any limitation on the present invention in any form, and the simple amendments, equivalent changes or modifications made by those skilled in the art using the technical contents disclosed shall all fall within the protection scope of the present invention.

What is claimed is:

1. A method of automatically tracing urine in a toilet, the method comprising:
    S1: acquiring an image of an interior of a toilet bowl through an image sensor on an inner side wall of the toilet, wherein the image of the interior of the toilet bowl comprises an image of urine or an image simultaneously showing the urine and a collecting and tracing member;
    S2: processing the image to identify a location of the urine or simultaneously identify the location of the urine and a location of the collecting and tracing member; and
    S3: moving the collecting and tracing member the identified location of the urine.

2. The method of claim 1, wherein:
    in S2, each pixel point in the acquired image is compared with a threshold value set through an image characteristic of the urine to identify the urine; or
    each pixel point in the acquired image is compared with threshold values respectively set through image characteristics of the urine and the collecting and tracing member to identify the urine and the collecting and tracing member.

3. The method of claim 2, wherein a background image is acquired before S1, and the background image is an image acquired when there is neither urine nor the collecting and tracing member in the interior of the toilet bowl; and
    in S2, the image is firstly processed to generate a difference image, and the difference image is a difference between the acquired image of the interior of the toilet bowl and the background image after the background image is acquired.

4. The method of claim 3, wherein:
in S2, binarization processing is conducted to the difference image to generate a binary image; and
a Hough transform is conducted to the binary image according to a characteristic function of the urine and a characteristic function of the collecting and tracing member, and a column number of the urine and a column number of the collecting and tracing member are identified according to a maximum value obtained from Hough transform of two sets of characteristic functions.

5. The method of claim 4, further comprising S4: repeating S1, S2, and S3 until the collecting and tracing member coincides with the urine in the image and the collecting and tracing member stops moving.

6. The method of claim 4, wherein the characteristic function of the urine describes a vertical line, and the characteristic function of the collecting and tracing member describes a geometric curve related to a position and a shape of the collecting and tracing member.

7. The method of claim 1, further comprising S4: repeating S1, S2, and S3 until the collecting and tracing member coincides with the urine in the image and the collecting and tracing member stops moving.

8. A device for automatically tracing urine, wherein the device is a smart toilet, an image sensor and a urine collection device are installed on an inner side wall of the smart toilet, a liquid collection head of the urine collection device is a collecting and tracing member, and the collecting and tracing member is used for tracing and collecting urine at the same time in the smart toilet based on an image captured by the image sensor.

9. The device of claim 8, further comprising a memory, a processor, and a computer program, wherein the computer program is stored in the memory and is executable on the processor, and wherein the processor implements a method of automatically tracing and collecting urine in the smart toilet in response to executing the computer program.

10. The device of claim 8, wherein the image sensor includes at least one of an infrared image sensor or a visible light image sensor.

11. The device of claim 8, wherein each of the image sensor and the urine collection device is installed on a left side wall or a right side wall of the smart toilet; or wherein each of the image sensor and the urine collection device is installed on a front side wall or a rear side wall of the smart toilet.

12. The device of claim 8, wherein the collecting and tracing member is provided with a color mark.

13. A method of automatically tracing and collecting urine in a smart toilet, the method comprising:
acquiring an image of an interior of a toilet bowl through an image sensor located on an inner side wall of the toilet bowl, wherein the image is configured to include urine from a user of the smart toilet and a collecting and tracing member of a urine collection device located in the toilet bowl;
identifying a location of the urine and a location of the collecting and tracing member through processing the image;
moving the collecting and tracing member to the urine in response to a result of the identification from the image; and
collecting a sample of the urine in a liquid collection head of the urine collection device.

14. The method of claim 13, wherein a background image is acquired through the image sensor before acquiring the image, and wherein the background image is acquired when there is no urine in the interior of the toilet bowl.

15. The method of claim 14, wherein the background image and the image are compared to generate a difference image showing a difference between the background image and the image of the interior of the toilet bowl after acquiring the background image.

16. The method of claim 15, wherein binarization processing is performed on the difference image to generate a binary image; and a Hough transform is conducted to the binary image according to a characteristic function of the urine and a characteristic function of the collecting and tracing member, and a column number of the urine and a column number of the collecting and tracing member are identified according to a maximum value obtained from the Hough transform.

17. The method of claim 16, wherein the characteristic function of the urine describes a vertical line, and the characteristic function of the collecting and tracing member describes a geometric curve related to a position and a shape of the collecting and tracing member.

18. The method of claim 17, further comprising repeating acquiring the image of the interior of the toilet bowl through the image sensor, simultaneously identifying the urine and the collecting and tracing member through processing the image, and implementing tracing movement to the urine by the collecting and tracing member in response to the result of the identification to the image, until the collecting and tracing member coincides with the urine in the image and the collecting and tracing member stops moving.

19. The method of claim 13, wherein each pixel point in the acquired image is compared with threshold values respectively set through image characteristics of the urine and the collecting and tracing member to identify the urine and the collecting and tracing member.

20. The method of claim 13, further comprising repeating acquiring the image of the interior of the toilet bowl through the image sensor, simultaneously identifying the urine and the collecting and tracing member through processing the image, and implementing tracing movement to the urine by the collecting and tracing member in response to the result of the identification to the image, until the collecting and tracing member coincides with the urine in the image and the collecting and tracing member stops moving.

* * * * *

UNITED STATES PATENT AND TRADEMARK OFFICE
CERTIFICATE OF CORRECTION

PATENT NO. : 11,119,091 B2  
APPLICATION NO. : 16/299773  
DATED : September 14, 2021  
INVENTOR(S) : Sun Page 1 of 1

It is certified that error appears in the above-identified patent and that said Letters Patent is hereby corrected as shown below:

In the Claims

Claim 1, Column 8, Line 51: add "to" after the word "member" and before the word "the identified".

Signed and Sealed this  
Twenty-eighth Day of December, 2021

Drew Hirshfeld  
*Performing the Functions and Duties of the*  
*Under Secretary of Commerce for Intellectual Property and*  
*Director of the United States Patent and Trademark Office*